United States Patent [19]
Dooley, Jr.

[11] Patent Number: 5,133,778
[45] Date of Patent: Jul. 28, 1992

[54] PROSTHETIC FOOT WITH DISPLACEABLE HEEL

[76] Inventor: John P. Dooley, Jr., 936 Moores Ct., Brentwood, Tenn. 37027

[21] Appl. No.: 666,134

[22] Filed: Mar. 7, 1991

[51] Int. Cl.⁵ .......................... A61F 2/66; A61F 2/62
[52] U.S. Cl. ........................................ 623/53; 623/38
[58] Field of Search ...................... 623/27, 38, 53-56

[56] References Cited

U.S. PATENT DOCUMENTS

| | | | |
|---|---|---|---|
| 468,352 | 2/1892 | Linkert | 623/53 |
| 598,458 | 2/1898 | Woodland | 623/53 X |
| 766,686 | 8/1904 | Gault | 623/55 X |
| 1,211,222 | 1/1917 | Pilling et al. | 623/53 X |
| 2,731,645 | 1/1956 | Woodall | 623/55 |
| 5,004,477 | 4/1991 | Palfray | 623/53 |

FOREIGN PATENT DOCUMENTS 0611553  7/1926  France ............................ 623/53

Primary Examiner—Randall L. Green
Assistant Examiner—David H. Willse
Attorney, Agent, or Firm—John A. Beehner

[57] ABSTRACT

A prosthetic foot apparatus with a movable heel to facilitate insertion of the heel into tight pants legs, boots, shoes and the like. The apparatus includes a generally stationary foot base and a heel connected thereto for movement between a normal walking position and a dressing position displaced forwardly and downwardly therefrom and a releasable locking means for retaining the heel in the walking position.

A method for moving the heel of a prosthetic foot to facilitate its insertion into tight pant legs, shoes, boots and the like includes: providing the prosthetic foot apparatus of the invention; releasing the locking means; allowing the heel to move forwardly and downwardly to the dressing position; inserting the foot apparatus into the pant leg, shoe, or the like; and returning the heel to the walking position by stepping down on the foot.

19 Claims, 5 Drawing Sheets

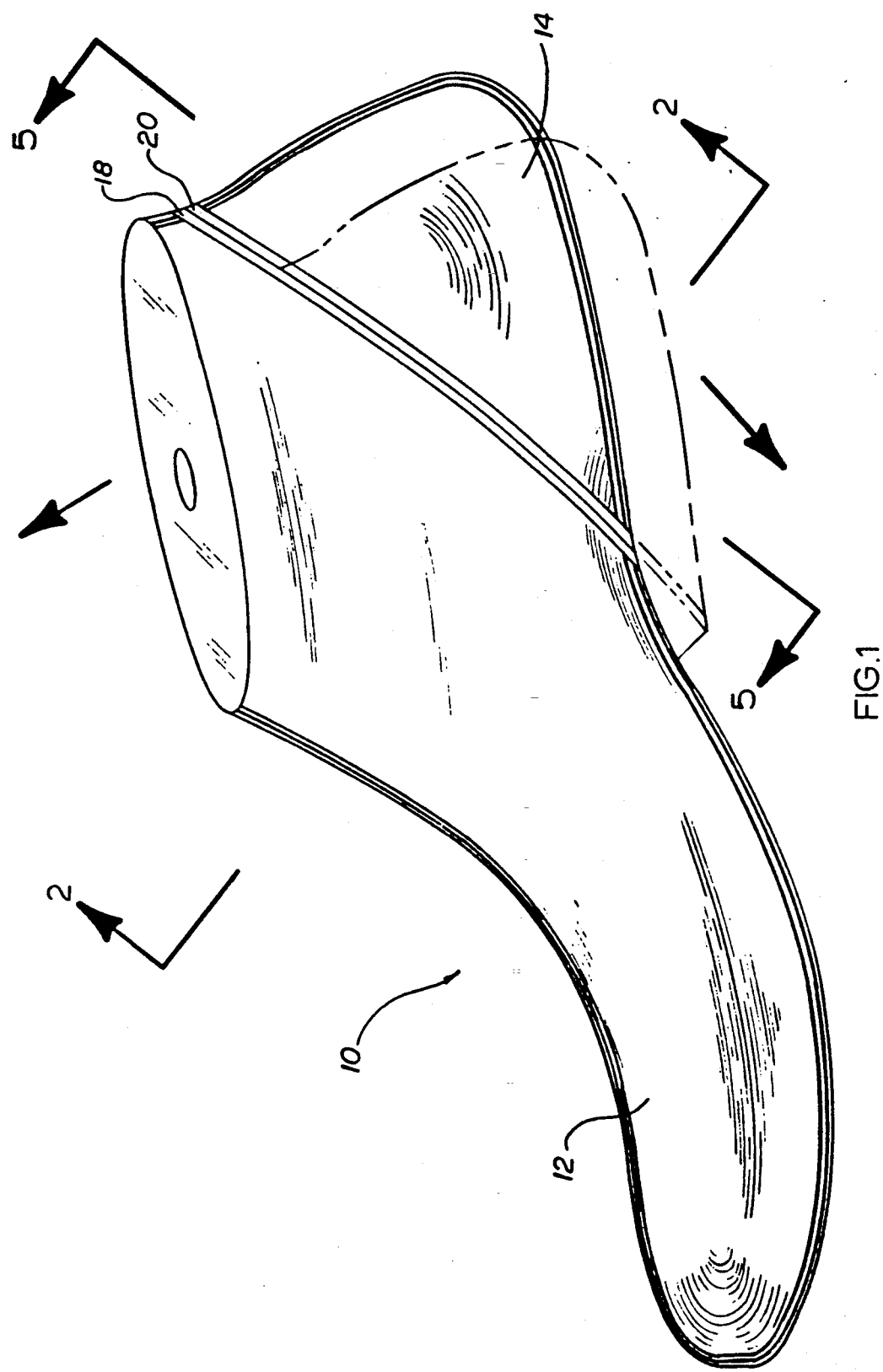

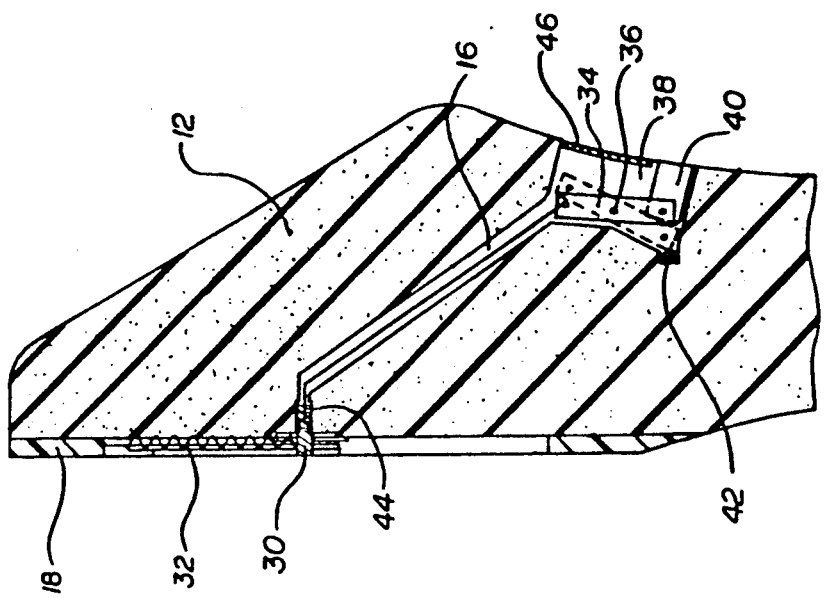
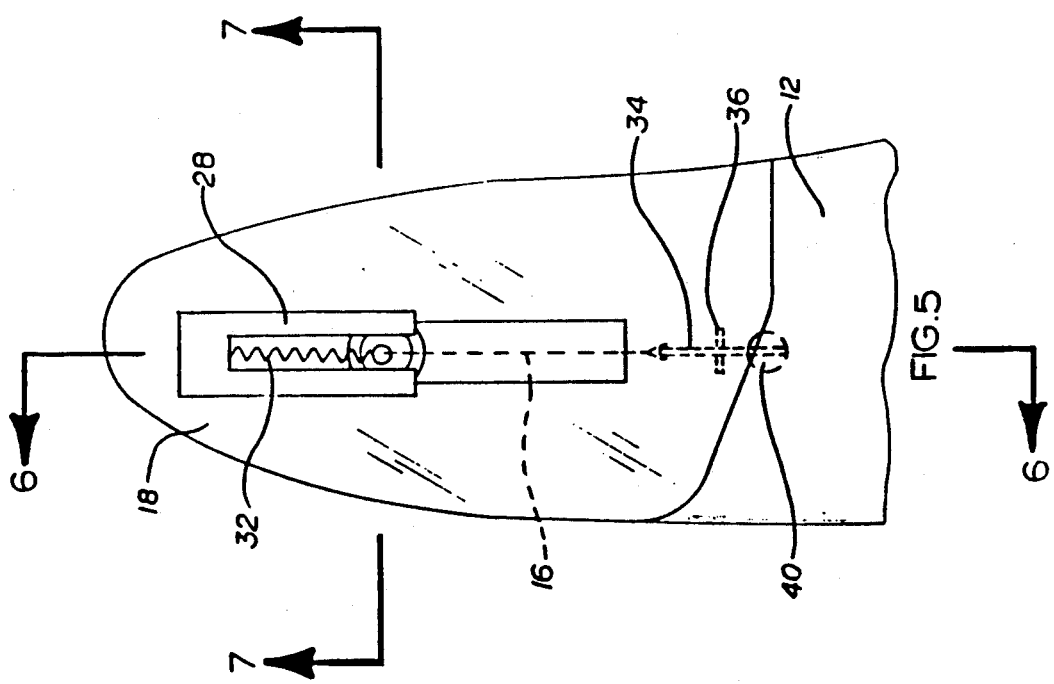

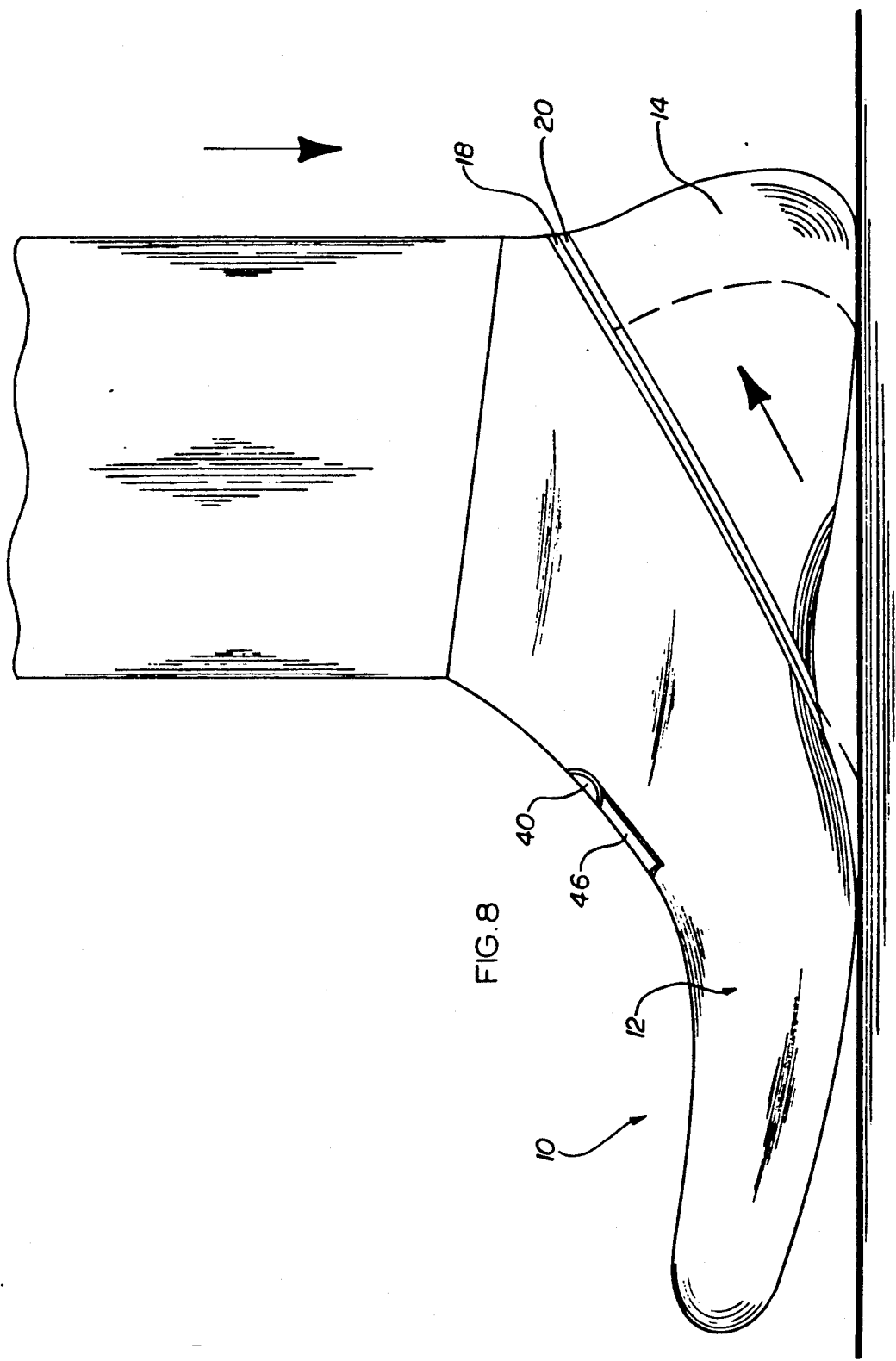

PROSTHETIC FOOT WITH DISPLACEABLE HEEL

BACKGROUND OF THE INVENTION

The present invention is directed generally to prosthetic legs and more specifically to a prosthetic foot having a displaceable heel to reduce the dimensions of the foot at times.

Prosthetic legs and associated devices have been in use for a long time and are well known in the art. Additionally, prosthetic feet having a rear portion of the heel hinged to facilitate walking are known in the art. However, movement of the heels in these devices is limited to the upward and downward directions and to a very limited distance of travel. None of the devices allow the heel of the foot to slide forward or to be removed.

Persons requiring the use of a prosthetic leg frequently have difficulty inserting the foot into a narrow pant leg. In addition to being time consuming and frustrating, the task can be physically demanding if the person is not able to move around with dexterity. Similarly, insertion of the foot into tight boots, shoes and the like is nearly impossible.

Accordingly, it is a primary objective of the present invention to provide a prosthetic foot having a stationary foot base and a moveable heel. Such moveable heel may be slidably moved substantially linearly forwardly and downwardly on the stationary foot base from a normal walking position to a dressing position, thus reducing the cross sectional area of the foot presented to the pants leg, boot and the like, and facilitating the insertion of the foot therein.

Another disadvantage of currently available prostheses is that a single foot design cannot be worn with all types of shoes. This lack of versatility may necessitate the acquisition and use of a new leg for each different shoe style or functional purpose. Accordingly, it is an additional objective of the present invention to provide a prosthetic foot with a removable heel. Thus, different shoe styles may be accommodated by the same leg, requiring only the heel be changed.

Another objective of the present invention is to provide a prosthetic foot which is inexpensive to manufacture.

Another objective of the present invention is to provide a prosthetic foot wherein the movable heel is readily locked in the normal walking position and wherein the release mechanism for the heel is self-contained with the foot.

Another objective of the present invention is to provide a prosthetic foot which is rugged in construction and easy to use.

SUMMARY OF THE INVENTION

The present invention teaches both a novel prosthetic foot apparatus and a novel method for inserting a prosthetic foot apparatus into narrow pants legs, tight boots, shoes and the like.

The prosthetic foot apparatus includes a stationary foot base, a movable heel and connecting means for movement of the heel relative to the foot base, from a normal walking position at the rearward end of the foot base, to a dressing position displaced forwardly and downwardly therefrom. The apparatus also includes a locking means operative to releasably retain the moveable heel in the walking position.

The locking means includes a pin retractably mounted in the foot base for retracting movement from a lower locked position to a raised release position. The locking means further includes a spring operatively associated with the pin for biasing the pin to the locked position. The locking means also includes an elongated tension member operatively connected to the pin for retracting the pin against the action of the spring. The tension member is preferably connected to an actuating lever within the foot base, which lever may be actuated by an externally accessible push button on the foot base.

One connection means includes a spring mounted adjacent the rearward end of the member and operative to urge the heel in its substantially forward and downward linear motion when the locking pin is retracted. The connection means also includes a stop shoulder which limits the travel of the heel downward and forward by engaging the locking pin during such sliding movement. The heel may be returned to the walking position simply by placing weight on the foot. Additionally, the heel may be completely removed from the stationary foot base by further retraction of the locking pin from the stop shoulder enabling further sliding movement of the heel past the stop shoulder.

The method for inserting a prosthetic foot apparatus into a shoe includes the steps of: providing the prosthetic foot apparatus of the present invention; releasing the locking means using the elongated tension member; allowing the heel to move linearly forwardly and downwardly to the dressing position, inserting the prosthetic foot apparatus into the shoe, boot or the like; stepping downward on the foot apparatus causing the heel to move upward and backward and ultimately locking in the walking position.

BRIEF DESCRIPTION OF THE DRAWINGS

FIG. 1 shows the prosthetic foot of the present invention, including both the movable heel and the stationary foot base, in a perspective view. The movable heel is shown in the walking position as a solid line and in the dressing position as a dotted line.

FIG. 5 is a bottom view of the rear portion of the stationary foot base showing the connection means and locking FIG. 6 is a cut-away side view of the rear portion of the stationary foot base.

FIG. 8 is a side view of the prosthetic foot attached to a prosthetic leg showing how the movable heel is returned to the walking position from the dressing position.

DESCRIPTION OF THE PREFERRED EMBODIMENT

Figure 3:
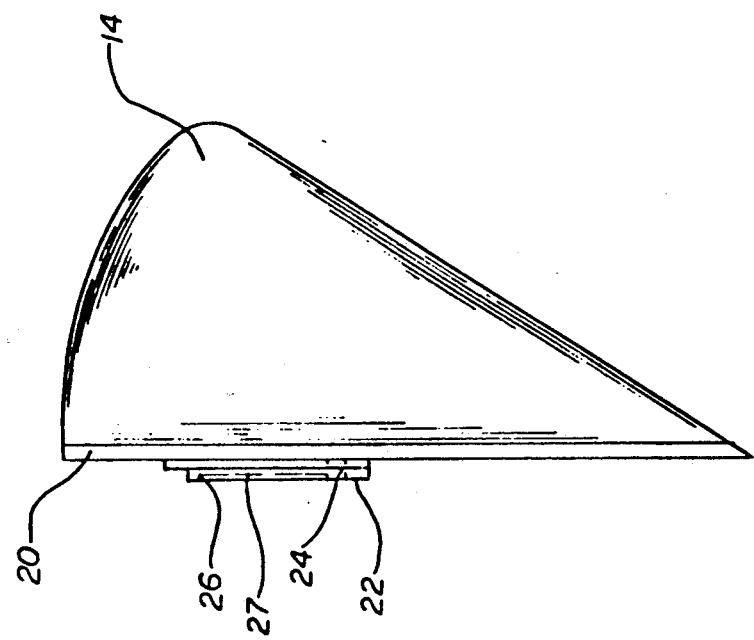
FIG. 3 is a side view of the movable heel.

The prosthetic foot with amovable heel 10 of the present invention is illustrated in FIG. 1 as having a stationary foot base 12 and a movable heel 14. The movable heel 14 is movable from the walking position, shown in solid line, to the dressing position, shown in dotted line. In the preferred embodiment, the stationary foot base 12 and the movable heel 14 would be constructed of generally available prosthetic construction material.

Also, shown in FIG. 1 is the stationary foot base attachment plate 18 and the movable heel attachment plate 20 which slides on the base attachment plate 18 for movement of the heel 14 between the walking and dressing positions. In the preferred embodiment, the attachment plates 18 and 20 are constructed of orthopedic casting material but other materials such as teflon might be used so long as they were substantially rigid and strong.

Figure 2:
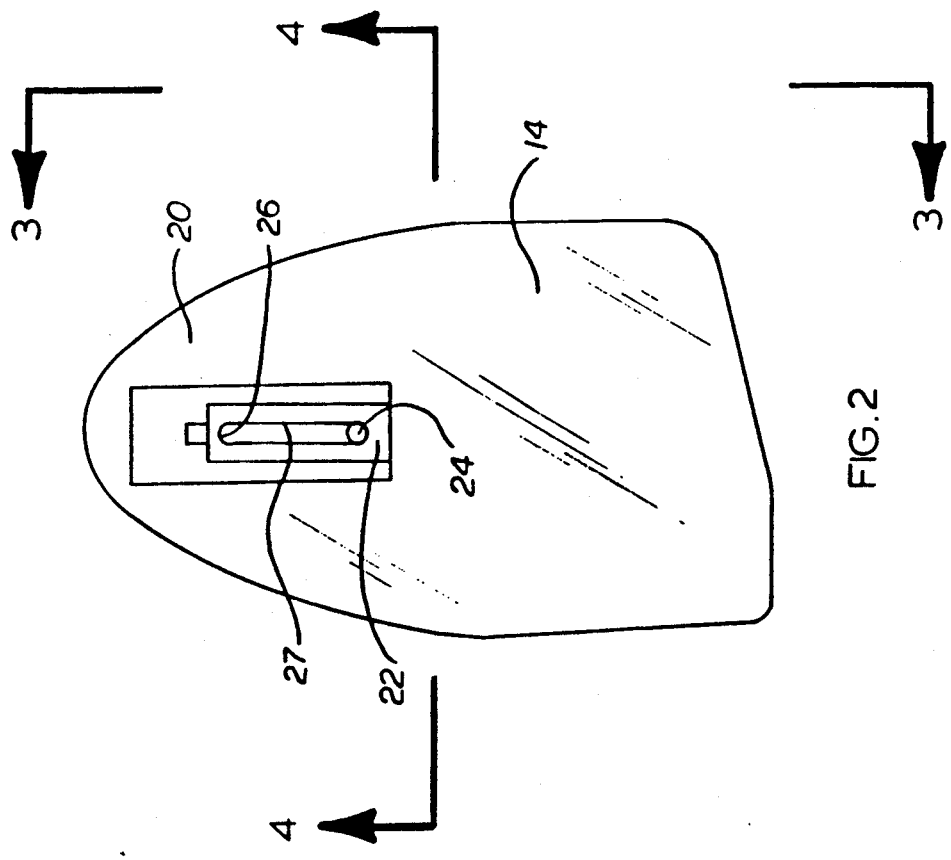
FIG. 2 is a top view of the movable heel.
Figure 4:
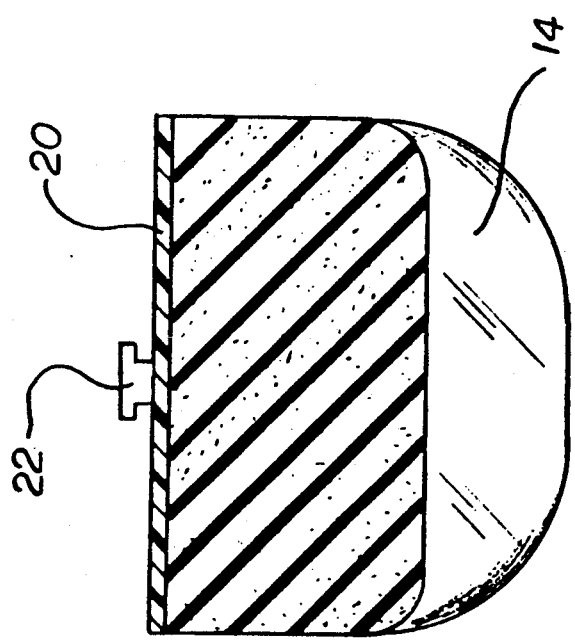
FIG. 4 is a rear elevational view of the movable heel.

FIG. 2, 3, and 4 show the movable heel 14, in top, side and rear views respectively. Shown in detail is the generally "T" shaped beam 22. FIG. 2 most clearly shows the generally "T" shaped beam 22 which includes an indentation 24, a circular hole in the illustrated embodiment, and a stop shoulder 26 at the opposite end of an open topped channel 27 extending from indentation 24. The indentation or hole 24 in beam 22 is operative to receive a locking pin 30 (shown in FIG. 6) upon movement of the movable heel 14 to the walking position thereby retaining the heel 14 in fixed relation to the stationary foot base 12 (shown in FIG. 1). The stop shoulder 26 is situated adjacent the rearward end of the "T" shaped beam 22 and is operative to engage the locking pin 30 (shown in FIG. 6) as the movable heel 14 slides substantially linearly, forwardly and downwardly to the dressing position of the movable heel 14 (shown as a dotted line in FIG. 1).

FIG. 5 shows the rear underside portion of the stationary foot base 12, looking at the attachment plate 18. A generally "C" shaped channel 28, is mounted substantially flush with the surface of the attachment plate 18 (FIGS. 6 and 7) and is constructed of a size and shape to be capable of receiving the "T" shaped beam 22 (FIG. 4) within the "C" channel 28. Also, shown are the locking pin 30 and the spring 32 shown in FIG. 5 in an extended position. The urging spring 32 is mounted adjacent the rear portion of the generally "T" shaped channel 28 and is operative to urge the generally "T" shaped beam 22 downwardly and forwardly to the dotted line dressing position in FIG. 1 when the locking pin 30 is retracted into the stationary foot base 12. The urging spring 32 is compressed when the generally "T" shaped beam 22 is retracted upwardly into the generally "C" shaped member 28. FIG. 5 also shows the recessed cavity 34 extended forwardly from the "C" shaped channel 28 and generally aligned therewith for receiving the heel upon sliding movement of the heel to the dressing position.

Figure 7:
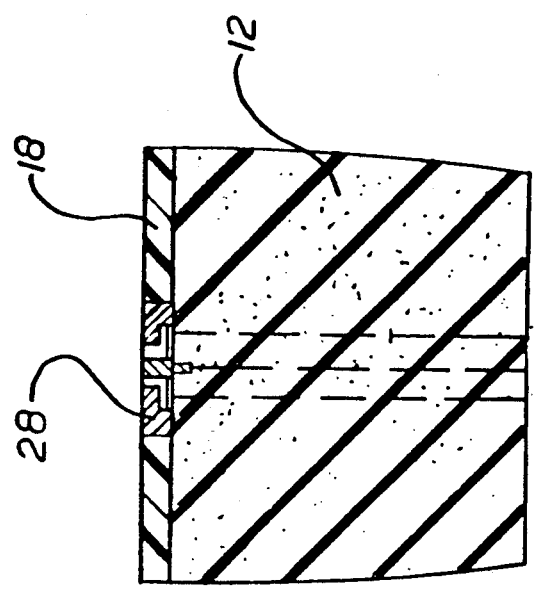
FIG. 7 is a rear cut-away view of the stationary foot base showing the locking means and substantially flush mounting of the connecting member.

FIG. 6 and 7 show cut-away side and rear views of the stationary foot base 12. The elongated tension member 16 is attached to the locking pin 30 and is operative to retract the pin 30 into the body of the stationary foot base 12 when the tension member 16 is pulled upwardly. In the preferred embodiment the elongated tension member 16 is a wire connected to a push button activated toggle or lever 34 for supplying the tension required to retract the pin 30.

Lever 34 is pivotally mounted by a transverse pivot pin 36 seated within a cavity 38 in the top 40 of the foot base 12. The forward end of the lever is connected to a push button 40 which is externally accessible through the top of the foot base for actuating lever 34. A return spring 42 within cavity 38 urges the rearward end of the lever toward its lowered locking position corresponding to the lowered locking position of pin 30. A corresponding return spring 44 engages the top of pin 30 to urge it downwardly to the locking position. When push button 30 is depressed, lever 34 pivots to the dotted line release position for likewise raising pin 30 to its release position. Upon release of the push button, the springs 42 and 44 return the lever 34 and pin 30 to their locking positions. A removable cover 46 may be snap fit onto cavity 38 to close it but for access to the push button 40.

When the movable heel 14 is in the walking position, locking pin 30 will be seated in the indentation 24 (FIG. 2) of the generally "T" shaped beam 22 (FIG. 2) thereby fixing the heel 14 into position. When it is desired that the heel 14 be slid forward into the dressing position (dotted line in FIG. 1), the elongated tension member 16 is pulled outwardly from the stationary foot base 12 causing the locking pin 30 to retract into the base 12 and disengage the indentation 24 (FIG. 2) in the generally "T" shaped beam 22 (FIG. 2). The disengagement of the pin 30 allows the urging spring 32 to expand, applying pressure on the generally "T" shaped beam 22, thereby causing it and the movable heel 14 to slide forwardly and downwardly within the generally "C" shaped channel 28. Forward sliding motion of the heel 14 continues until the stop shoulder 26 (FIG. 2), adjacent the rear of the generally "T" shaped beam 22, engages the partially retracted locking pin 30 thereby stopping movement of the heel 14 at the dressing position.

If the movable heel 14 is to be removed after being moved into the dressing position, the locking pin 30 is further retracted into the foot base 12 by the elongated tension member 16 thereby enabling movement of the stop shoulder 26 past the locking pin 30.

FIG. 8 shows the procedure for returning the heel 14 to the walking position from the dressing position. When the prosthetic foot 10 has been inserted into the pant leg, shoe, boot or the like, and the heel 14 is to be returned to the walking position, pressure is applied to the underside of the foot 10. Applying pressure to the underside of the foot 10 causes the heel 14 to slide upwardly and rearwardly until the locking pin 30 engages the indentation 24 (FIG. 2) in the generally "T" shaped beam 22, locking movable heel 14 in the walking position.

Whereas the invention has been shown and described in connection with a preferred embodiment thereof, it is apparent that many modifications, additions and substitutions may be made which are within the intended broad scope of the appended claims. For example, various means for retracting the locking pin may be employed and alternate locking systems for the movable heel may be devised.

Thus there has been shown and described a prosthetic foot apparatus which accomplishes at least all of the stated objectives.

I claim:

1. A prosthetic foot apparatus adapted to facilitate insertion thereof into tight pant legs, boot, shoes and the like, comprising:
   a stationary foot base;
   a movable heel; and
   connecting means for connecting said movable heel to said stationary foot base for movement of said heel, relative to said stationary foot base, from a normal walking position at a rearward end of said foot base to a dressing position displaced forwardly and downwardly therefrom,
   said connecting means connecting said heel to said foot base for sliding movement between said walking and dressing positions.

2. The invention of claim 1 wherein said connecting means constrains said movable heel to substantially linear sliding movement between said walking and dressing positions.

3. The invention of claim 1 further comprising coacting locking means for retaining said movable heel in substantially fixed relation to said stationary foot base upon movement of said movable heel to said walking position.

4. The invention of claim 3 further comprising coacting travel limiting means on said heel and foot base and operative to limit said linear forward and downward sliding movement of said movable heel to said dressing position.

5. The invention of claim 3 wherein said connecting means comprises,
    a generally "C" shaped channel secured to one of said heel and foot base;
    a generally "T" shaped beam secured to the other of said heel and foot base;
    said "C" and "T" shaped channel and beam being constructed in such shape and size that said "T" shaped beam is receivable within said "C" shaped channel for sliding movement relative thereto.

6. The invention of claim 5 wherein said locking means comprises:
    a pin retractably mounted on said foot base for retracting movement from a lowered locking position to a raised release position,
    said heel including an indentation positioned for receiving said pin upon movement of said heel to the walking position thereof,
    a spring operatively associated with said pin for biasing said pin toward the locking position; and
    retracting means operatively connected to said pin for retracting said pin from said locking position against the action of said spring.

7. The invention of claim 6 wherein said retracting means comprises an elongated tension member connected to said pin.

8. The invention of claim 7 wherein said retracting means further comprises a lever mounted within said foot base and having a free end connected to said elongated tension member, said lever being pivotally movable with said pin between a lowered locking position and a raised released position for controlling movement of the pin.

9. The invention of claim 8 further comprising means biasing said lever to the lowered locking position thereof.

10. The invention of claim 8 further comprising a push button connected to said lever and accessible through an opening in said foot base for pivotally moving said lever to raise and lower said pin.

11. The invention of claim 10 wherein said lever is mounted within a cavity in said foot base.

12. The invention of claim 6 wherein said "T" shaped beam is secured to said heel and said indentation is formed in said "T" shaped beam.

13. The invention of claim 12 further comprising a spring mounted adjacent the rear of said "C" shaped channel and being operative to urge said "T" shaped beam and said movable heel in said substantially linear forward and downward direction.

14. The invention of claim 13 wherein said coacting travel limiting means comprises said pin and a stop shoulder located adjacent a rearward end of said "T" shaped beam and positioned for engagement with said locking pin upon forward and downward sliding movement of said movable heel to said dressing position.

15. The invention of claim 14 wherein said locking pin is retractable from said stop shoulder to enable sliding movement of said stop shoulder past said locking pin for detaching said heel from said foot base.

16. The invention of claim 15 wherein said "C" shaped channel is recessed into said foot base such that it is substantially flush with the surface of said stationary foot base, said stationary foot base having a recessed cavity extended substantially forwardly from said "C" shaped channel and generally aligned therewith for receiving said "T" shaped beam upon sliding movement of said heel to the dressing position.

17. A method for facilitating the insertion of a prosthetic foot into tight pant legs, boots, shoes and the like, comprising:
    providing a prosthetic foot including a generally stationary foot base and a heel connected thereto for movement between a normal walking position and a dressing position displaced forwardly and downwardly therefrom, and releasable locking means for retaining said heel in the walking position;
    releasing the locking means;
    moving the heel from said walking position to said dressing position;
    inserting the prosthetic foot into the pant leg, boot or the like; and
    stepping on the foot, thereby returning the heel to the walking position and engaging said locking means.

18. The invention of claim 17 wherein said moving step comprises sliding said heel in a substantially linear direction forward and downward.

19. The invention of claim 18 wherein said locking means comprises an elongated tension member connected to a retractable pin on said foot base and said releasing step comprises retracting said pin with elongated tension member.

* * * * *